US005789580A

United States Patent [19]
Chambers et al.

[11] Patent Number: 5,789,580
[45] Date of Patent: Aug. 4, 1998

[54] SELECTIVELY FLUORINATED ORGANIC COMPOUNDS

[75] Inventors: Richard Dickinson Chambers; Graham Sandford, both of Durham, United Kingdom

[73] Assignee: British Nuclear Fuels plc, Warrington, England

[21] Appl. No.: 619,498

[22] PCT Filed: Jul. 26, 1995

[86] PCT No.: PCT/GB95/01765

§ 371 Date: Apr. 25, 1996

§ 102(e) Date: Apr. 25, 1996

[87] PCT Pub. No.: WO96/03357

PCT Pub. Date: Feb. 8, 1996

[30] Foreign Application Priority Data

Jul. 26, 1994 [GB] United Kingdom ............... 9414974

[51] Int. Cl.$^6$ ............... C07H 1/00; C07B 39/00; C07C 17/093

[52] U.S. Cl. ............... 536/124; 536/18.4; 536/122; 570/161; 570/164; 570/165; 570/252; 570/253

[58] Field of Search ............... 536/18.4, 18.5, 536/122, 124; 570/123, 124, 127, 140, 142, 161, 164, 165, 252, 253

[56] References Cited

PUBLICATIONS

*Monosaccharides: Their Chemistry and Their Roles in Natural Products*, Ed. by Collins & Ferrier, (John Wiley & Sons, Ltd.: West Sussex, England), pp. 97–100, (1995).
Roush et al., *J. Org. Chem.*, vol. 56:1649–1655, (1991).
Nicolaou et al., *J. Amer. Chem. Soc.*, vol. 106:4189–4192, (1984).

*Primary Examiner*—John Kight
*Assistant Examiner*—Howard C. Lee
*Attorney, Agent, or Firm*—Sheridan Ross P.C.

[57] ABSTRACT

A process for the preparation of a selectively fluorinated organic compound, which process includes reaction of a precursor of said organic compound, the precursor containing at least one Group VI element selected from sulfur, selenium and tellurium, with a fluorinating agent and another halogenating agent and characterized in that the fluorinating agent is elemental fluorine.

18 Claims, No Drawings

SELECTIVELY FLUORINATED ORGANIC COMPOUNDS

FIELD OF THE INVENTION

The present invention relates to selectively fluorinated organic compounds and their preparation.

BACKGROUND AND SUMMARY OF THE INVENTION

The selective fluorination of organic molecules has received considerable attention because of the profound effect that fluorine can have on the physical, chemical and biological properties of a wide range of substrates. For example, the introduction of a difluoromethylene unit into a molecule is an important target since the $CF_2$ group is isopolar and isosteric with an ether oxygen and has a steric profile not dramatically different to that of a methylene group. Consequently, effective methods for constructing fluorine containing groups such as fluoromethyl, difluoromethylene or trifluoromethyl from readily available, cheap fluorinating agents are highly desirable and many reagents have been developed in order meet these targets.

DETAILED DESCRIPTION OF THE INVENTION

The fluorination of sulfur containing substrates offers an attractive route to fluoromethyl, difluoromethylene or trifluoromethyl containing substrates as many sulfur containing organic compounds are readily available from inexpensive starting materials by well established chemistry. Several methods for the fluorodesulfurization of organic compounds have been devised.

These reactions are generally performed by reacting the appropriate sulfur containing substrate with a combination of a source of electrophilic halogen such as N-bromosuccinimide with a fluoride ion donor such as pyridinium poly(hydrogen fluoride). Thus, fluoromethyl containing substrates may be prepared by treating a phenyl thioglycoside with diethylaminosufur trifluoride and N-bromosuccinimide. Difluoromethylene containing substrates may be prepared by reacting a 1,3-dithiolane with N-bromosuccinimide and pyridinium poly(hydrogen fluoride) or upon reaction with difluoroiodobenzene. Trifluoromethyl containing substrates may be prepared by treating an orthothio ester with N-bromosuccinimide and pyridinium poly(hydrogen fluoride). However, many of these reagents suffer from the disadvantages of being difficult to handle, they may be highly toxic and may be expensive.

The fluorination of thiocarbonyl containing substrates offers an attractive route to gem-difluoromethylene compounds as such substrates can readily be prepared from aldehydes or ketones by well established routes.

Only a few methods for the fluorodesulfurization of thiocarbonyl containing substrates are known. These typically involve the synthesis of α,α-difluoroethers from thioesters upon reaction with diethylaminosulfur trifluoride (DAST) or with bromine trifluoride. No extension of these methods to other thiocarbonyl derivatives has been proposed and, in addition, the reagents used are toxic, are difficult to handle and may be expensive.

According to the present invention there is provided a process for the preparation of a selectively fluorinated organic compound, which process includes the reaction of a precursor of the said organic compound, the precursor containing at least one group VI element selected from sulfur, selenium and tellurium, with a fluorinating agent and another halogenating agent and characterised in that the fluorinating agent is elemental fluorine.

The group VI containing precursor may be a thiocarbonyl containing substrate.

The group VI containing precursor may be contained in an inert solvent.

Preferably, the inert solvent may be a neutral substance such as acetonitrile and desirably may be a polar solvent such as dichloromethane or chloroform or an acid such as sulfuric acid or trifluoroacetic acid.

The halogenating agent may comprise elemental iodine or bromine or an interhalogen compound. The interhalogen compound may comprise iodine monochloride or iodine monobromide.

The process according to the present invention may be carried out by passing fluorine gas into the group VI containing precursor in solution in a suitable vessel. Alternatively, a flowing stream of the solution may be contacted with a gaseous flow of fluorine in countercurrent fashion.

The reaction of the process may be carried out at a temperature in the range –60° C. to +150° C. although a temperature of from –20° C. to +50° C. is preferred.

Preferably, the fluorine gas is diluted before use by mixing with an inert gas such as nitrogen or helium. The concentration of fluorine in the inert gas may be from 1% to 50% by volume, preferably from 2% to 25% by volume, and especially from 5% to 15% by volume.

When the fluorination reaction of the process is complete, the selectively fluorinated organic compounds may be isolated by purging the reaction mixture with an inert gas to remove any residual fluorine gas or hydrogen fluoride formed during the reaction, followed by dilution with an excess of aqueous sodium metabisulphite solution and extraction of the selectively fluorinated organic compounds into a suitable solvent followed by purification by distillation or column chromatography.

Surprisingly and beneficially the inventors have found that elemental fluorine can be used to convert sulfur containing substrates into corresponding fluoro, difluoro, or trifluoro compounds by relatively simple route using readily available, inexpensive starting materials. In addition, elemental fluorine, when used in conjunction with a halogen such as iodine, permits the difluorination of a wide range of thiocarbonyl derivatives at room temperature in common organic solvents by a process which does not suffer from any of the disadvantages of the methods previously applied to the difluorination of thiocarbonyls. The use of elemental fluorine for the singe specific fluorination of organic compounds is rarely satisfactory due to the high reactivity of the element which may cause side reactions. However, in the case of the present invention, the reaction required can be controlled by selection of the rate of fluorine gas applied to the reaction.

The process of the present invention may be used to convert a wide range of compounds containing group VI elements, especially sulfur, to the corresponding fluorinated analogues. In particular, the preparation of fluorine containing compounds of formulae (1), (2), (3), (4) or (5) as follows:

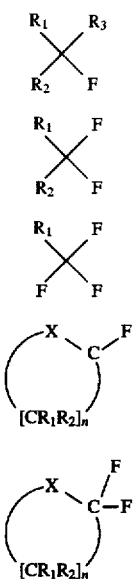

comprises converting the corresponding precursor compounds of formulae (6), (7), (8), (9), (10), (11) or (12) as follows:

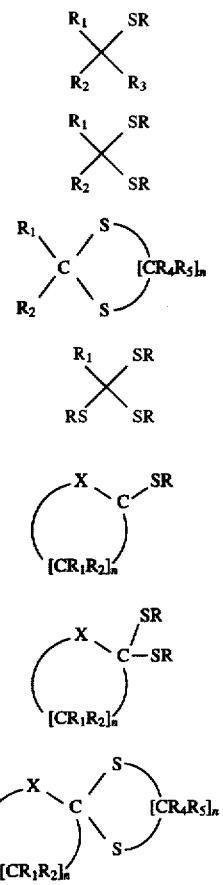

into the compounds (1), (2), (3), (4) or (5) by reaction with elemental fluorine as described hereinbefore.

The groups $R_1$, $R_2$ and $R_3$ may be selected from hydrogen, alkyl, substituted alkyl, cycloalkyl, substituted cycloalkyl, aryl, substituted aryl, or acetoxy. Where any of the groups $R_1$, $R_2$ or $R_3$ is an alkyl, cycloalkyl, or aryl substitutent, the said group may include one or more optional substituents or hetero atoms.

The groups R, $R_4$, and $R_5$ may be selected from hydrogen, alkyl, cycloalkyl, aryl or substituted aryl.

The substituent X may include oxygen, NH, NR or sulfur.

The structures represented by formulae (4), (5), (8), (10), (11) and (12) are cyclic and n may be an integer in the inclusive range from 1 to 8.

In carrying out the reaction, the ratio of fluorine to compound of formula (6) or (10) may be varied within wide limits although it is preferred that the molar ratio is in the range 0.5 to 2.0:1, especially 1.1 to 1.25:1 (fluorine: organic compound). The ratio of fluorine to compound of formula (7), (8), (11) or (12) may be varied within wide limits although it is preferred that the molar ratio is in the range 1.5 to 2.5:1, especially 2.0 to 2.25:1 (fluorine: organic compound). The ratio of fluorine to compound of formula (9) may be varied within wide limits although it is preferred that the molar ratio is in the range 2.5 to 3.5:1, especially 3.1 to 3.25:1 (fluorine:organic compound).

The ratio of halogen or interhalogen to compound of formula (6) or (10) may be varied within wide limits although it is preferred that the molar ratio is in the range 0.5 to 2.0:1, especially 1.1 to 1.25:1 (halogen/interhalogen:organic compound). The ratio of halogen or interhalogen to compound of formula (7), (8), (11), or (12) may be varied within wide limits although it is preferred that the molar ratio is in the range 1.5 to 2.5:1, especially 2.0 to 2.25:1 (halogen/interhalogen:organic compound). The ratio of halogen or interhalogen to compound of formula (9) may be varied within wide limits although it is preferred that the molar ratio is in the range 2.5 to 3.5:1, especially 3.1 to 3.25:1 (halogen/interhalogen:organic compound).

The process according to the present invention therefore provides an inexpensive and convenient synthetic route to fluorine containing organic compounds.

The process of the present invention may also be used to convert a wide range of thiocarbonyl compounds to the corresponding difluorinated analogues. In particular, the preparation of difluorinated compounds of formulae (13) or (14) as follows:

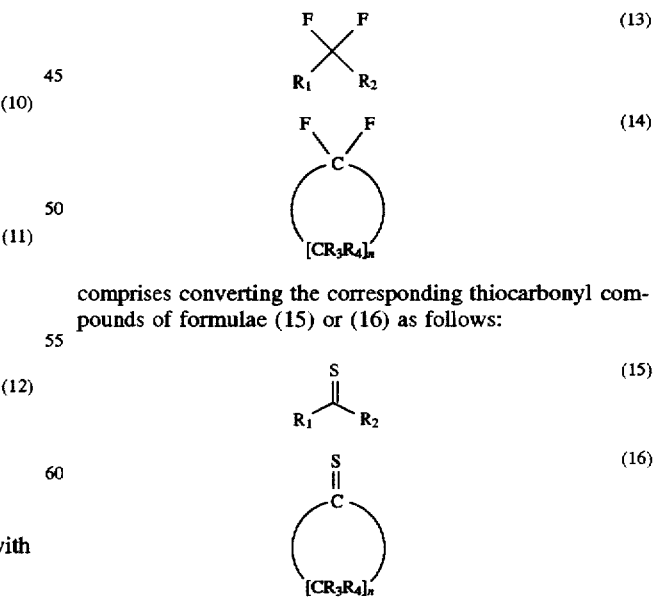

comprises converting the corresponding thiocarbonyl compounds of formulae (15) or (16) as follows:

into the compounds (13) or (14) by reaction with elemental fluorine as described hereinbefore.

The groups $R_1$, $R_2$, $R_3$ and $R_4$ may be selected from hydrogen, alkyl, substituted alkyl, cycloalkyl, substituted cycloalkyl, perfluoroalkyl, substituted perfluoroalkyl, aryl, substituted aryl or acetoxy. Where any of the groups $R_1$, $R_2$, $R_3$ or $R_4$ is an alkyl, cycloalkyl or aryl substituent, the said group may include one or more optional, substituents or hetero atoms.

The structures represented by formulae (14) and (16) are cyclic and n may be an integer in the inclusive range from 1 to 8.

In carrying out the reaction, the ratio of fluorine to compound of formula (15) or (16) may be varied within wide limits although it is preferred that the molar ratio is in the range 1.5 to 2.5:1, especially 2.0 to 2.25:1 (fluorine:organic compound).

The ratio of halogen or interhalogen to compound of formula (15) or (16) may be varied between wide limits although it is preferred that the molar ratio is in the range 1.5 to 2.5:1, especially 2.0 to 2.25:1 (halogen/interhalogen:organic compound).

The process according to the present invention therefore additionally provides an inexpensive and convenient synthetic route to difluoromethene containing organic compounds.

Embodiments of the present invention will now be described, by way of example only, with reference to the following Examples:

EXAMPLE 1

Preparation of 1-(difluorophenylmethyl)-2,4-dimethylbenzene

A solution 2-phenyl-2-(2',4'-dimethylphenyl)-1,3-dithiolane (2.4 g, 8.5 mmol), iodine (4.3 g, 17 mmol) and acetonitrile (40 ml) was placed in a PTFE fluorination vessel with attached soda lime filled drying tube. Fluorine gas (17 mmol) as a 10% mixture in nitrogen was then passed through the stirred solution using narrow bore PTFE tubing at ca 4.0 ml/min. The mixture was added to a 10% sodium metabisulfite solution (50 ml), extracted with dicloromethane (3×50ml), dried ($MgSO_4$) and evaporated. Column chromatography on silica gel using 9:1 hexane/ether as the eluant gave pure 1-(difluorophenylmethyl)-2,4-dimethylbenzene which was obtained as a clear liquid in 65% isolated yield; $\delta H$ (250 MHZ, $CDCl_3$, $Me_4Si$) 2.15 ppm (3H, s, $CH_3$), 2.31 (3H, s, $CH_3$), 6.9–7.4 (8H, m, Ar-H); $\delta F$ (235 MHZ, $CDCl_3$, $CFCl_3$) –86.7 ppm (s); m/z (EI+) 232 ($M^+$, 100%), 217 (24), 211 (21), 197 (33), 154 (89), 127 (27), 105 (16), 77 (15); as compared to the literature data.

EXAMPLE 2

Preparation of 1-(difluorophenylmethyl)-4-bromobenzene

In a similar reaction to that described in Example 1, 2-phenyl-2-(4' bromophenyl)-1,3-dithiolane gave 1-(difluorophenylmethyl)-4-bromobenzene as a clear liquid in 61% isolated yield: $\delta H$ (250 MHz, $CDCl_3$, $Me_4Si$) 7.32–7.52 ppm (m, Ar-H); $\delta F$ (235 MHz, $CDCl_3$, $CFCl_3$) –89.5 ppm (s); $\delta C$ (100 MHz, $CDCl_3$, $Me_4Si$) 120.37 ppm (t, $^1J$ 242, $CF_2$), 124.4 (t, $^4J$ 2.3, C-3"), 125.8 (t, $^3J$ 5.7, C-2"), 127.6 (t, $^3J$ 5.5, C-2'), 120.5 (s, C-4"), 130.1 (t, $^4J$ 1.9, C-3'), 131.7 (s, C-Br), 136.9 (t, $^2J$ 29, C-1"), 137.3 (t,$^2J$ 28.3, C-1'); m/z ($EI^+$)282 ($M^+$, 21%), 284 (M++2.24), 205 (20), 203 (36), 185 (39), 183 (100), 127(35), 105 (42); as compared to the literature data.

EXAMPLE 3

Preparation of 1-(difluoro-4-fluoronhenylmethyl)-4-fluorobenzene

In a similar reaction to that described in Example 1, bis (4'-fluorophenyl)-1,3-dithiolane gave 1-(difluoro-4-fluorophenyl-methyl)-4 fluorobenzene as a clear liquid in 66% isolated yield; $\delta H$ (100 MHz, $CDCl_3$, $Me_4Si$) 7.06 ppm (4H, m, Ar-H), 7.45 (4H, m, Ar-H); $\delta F$ (235 MHz, $CDCl_3$, $CFCl_3$) –86.8 (2F, s, $CF_2$), –111.0 (2F, s Ar-F); $\delta C$ (100 MHZ, $CDCl_3$, $Me_4Si$) 115.62 (d, $^2J$ 22.0, C-3), 120.20 (t, $^1J$ 241.8, $CF_2$), 128.16 (d t, $^3J$ 8.4 and 5.5, C-2)), 123.63 (t d, $^2J$ 28.9, $^4J$ 3.4, C-1), 163.74 (d t, $^1J$ 250.2, $^5J$ 2.0, C-4); m/z ($EI^+$) 240 ($M^+$, 100%), 221 (27), 218, (26), 201 (13), 145 (80), 123 (39), 95 (57); as compared to the literature data.

EXAMPLE 4

Preparation of difluorodiphenylmethane

In a similar reaction to that described in Example 1, benzothiophenone gave difluorodiphenylmethane as a clear liquid in 56% isolated yield; $\delta_H$ (250 MHZ, $CDCl_3$, $Me_4Si$) 8.43 ppm (m, Ar-H); $\delta_F$ (235 MHz, $CDCl_3$, $CFCl_3$ –89.2 ppm (s) m/z ($EI^+$) 204 (M+, 100%), 183 (37), 127 (89), 77 (23); as compared to the literature data.

EXAMPLE 5

Preparation of 9,9-difluoro-9H-fluorene

In a similar reaction to that described in Example 1, 9H-fluoroenyl-1,3-dithiolane gave 9,9-difluoro-9H-fluorene as a white solid in 52% isolated yield; $\delta_H$ (250 MHz, $CDCl_3$, $Me_4Si$) 7.35–7.7 ppm (m, Ar-H); $\delta_F$ (235 MHz, $CDCl_3$, $CFCl_3$) –112.1 ppm; $\delta_C$ (100 MHz, $CDCl_3$, $Me_4Si$) 120.35 ppm (s, Ar-H), 123.22 (t, $^1J$ 242.6, $CF_2$), 123.80 (s, Ar-H), 128.76 (s, Ar-H), 132.00 (s, Ar-H), 138.04 (t, $^2J$ 25.1, C-1), 139.50 (t, $^3J$ 5.1, C-2); m/z ($EI^+$) 202 (M+, 55%), 201 (100), 183 (41), 181 (21), as compared to the literature data.

EXAMPLE 6

Preparation of 1-(difluorophenylmethyl)-4-chlorobenzene

In a similar reaction to that described in Example 1, 2-phenyl-2-(4'-chlorophenyl)-1,3-dithiolane gave 1-(difluorophenylmethyl-4-chlorobenzene as a clear liquid in 64% isolated yield; $\delta_H$ (250 MHz, $CDCl_3$, $Me_4Si$) 7.64 (m, Ar-H); $\delta_F$ (235 MHz, $CDCl_3$, $CFCl_3$) –89.2 ppm (s); m/z ($EI^+$) 238 ($M^+$, 100%), 240 ($M^+$ 2, 27), 219 (14), 203 (99), 183 (44), 163 (20), 161 (52), 127 (41), 77 (11), as compared to the literature data.

EXAMPLE 7

Preparation of β-D-glucopyranosyl fluoride tetraacetate

Elemental fluorine gas (3.4 mmol diluted to a 10% solution in nitrogen) was bubbled slowly through a mixture of phenyl-1-thio-β-D-glucopyranoside tetraacetate (0.75 g, 1.7 mmol) and iodine (0.86 g, 3.4 mmol) in dry acetonitrile (15 ml). After the addition of fluorine was complete the solution was poured into 10% sodium metabsulfite and extracted with dichloromethane. The organic layer was washed sequentially with 10% sodium bicarbonate and water, dried ($MgSO_4$) and evaporated to a thick yellow syrup. $^{19}F$ nmr analysis of the product mixture showed the presence of both anomers with ratio α:β=1:6. Purification of the product mixture by column chromatography on silica gel with ethyl acetate: petroleum ether (1:1) as eluant yielded pure β-D-glucopyranosyl fluoride tetraacetate (320mg, 54%) as white crystals; m.p. 87°–88° C. from ether |lit. 89° C.|; $[\alpha]_D$+20.8 (lit., $[\alpha]_D$ 20.0); $R_F$ 0.52; (Found: C. 47.7; H.

5.55. Calc. for $C_{14}H_{19}O_9F$: C, 48.0, H, 5.4%); $\delta_H$ (400 MHz, CDCl$_3$, Me$_4$Si) 2.04, 2.05, 2.10, 2.11 (each 3H, s, CH$_3$ groups), 3.90 (1H, d d d, $J_{4,5}$ 9.4, $J_{5,6a}$ 4.8, $J_{5,6b}$ 2.8, H-5), 4.22 (1H, d d, $J_{6a,6b}$ 12.4, $J_{5,6b}$ 2.8, H-6b), 4.27 (1H, d d, $J_{6a,6b}$ 12.4, $J_{5,6a}$ 4.4, H-6a), 5.11 (1H, m, H-2), 5.21 (2H, m, H-3,4), 5.37 (1H, d d, $^1J_{H,F}$ 52.4, $J_{H1,H2}$ 5.4, H-1); $\delta_C$ (100 MHz, CDCl$_3$, Me$_4$Si) 20.6 ppm and 20.7 (s, CH$_3$ groups overlapping), 61.7 (s, C-6), 67.4 (s, C-4), 71.1 (d, $^2J_{C,F}$ 28.6, C-2), 71.8 (d, $^3J_{C,F}$ 8.4, C-3), 72.0 (d, $^3J_{C,F}$ 4.2, C-5), 106.2 (d, $^1J_{C,F}$ 219.7, C-1), 169.1, 169.3, 170.0 and 170.6 (s, C=O groups); $\delta_F$ (235 MHz, CDCl$_3$, Me$_4$Si) −141.88 ppm (d d, $^1J_{H,F}$ 53.0, $^2J_{H,F}$ 12.5, F-1); r/z (Cl$^+$, NH$_3$) 331 (M$^+$–F, 100%)

EXAMPLE 8

Preparation of 4-O-(2,3,4,6-tetra-O-acetyl-α-D-glucopyranosyl)-β-D-glucopyranosyl fluoride triacetate In a similar reaction to that described in Example 7, but using phenyl-4-O-(2,3,4,6-tetra-O-acetyl-α-D-glucopyranosyl)-1-thio-β-D-glucopyranoside triacetate as the starting material, $^{19}$F nmr analysis of the crude product mixture obtained showed the presence of both fluoro-anomers with α:β ratio 1:10. Purification of the product mixture by column chromatography on silica gel with ethyl acetate: petroleum ether (7:3) as eluant yielded pure 4-O-(2,3,4,6-tetra-O-acetyl-α-D-glucopyranosyl)-β-D-glucopyranosyl fluoride triacetate (375 mg, 57%) as white crystals: R$_F$ 0.62; $\delta_H$ (400 MHz, CDCl$_3$, Me$_4$Si) 2.01, 2.03, 2.05, 2.06, 2.10, 2.11 and 2.12 (each 3H, s, CH$_3$ groups), 3.99 (1H, m, H-5'), 4.01 (1H, mn, H-5), 4.08 (1H, d d, $J_{H6a',H6b'}$ 12.4, $J_{H5',H6a'}$, 2.4, H-6a') 4.16 (1H, t, $J_{H4,H5}$ 8.4, H-4'), 4.22 (1H, d d, $J_{H6a',H6b'}$ 12.0, $J_{H5,H6b}$ 4.4, H-6b), 4.25 (1H, d d, $J_{H6a',H6b'}$, 12.8, $J_{H5',H6b'}$ 4.0, H-6b'), 4.55 (1H, d d, $J_{H6a,H6b}$ 12.0, $J_{H5,H6a}$ 3.2, H-6a), 4.85 (1H, d d, $J_{H2',H3'}$ 10.8, $J_{H1',H2'}$ 4.0, H-2'), 4.95 (1H, m, H-2), 5.07 (1H, t, $J_{H4',H5'}$ 10.0, H-4'), 5.14 (1H, t, $J_{H3,H4}$ 7.0, H-3), 5.38 (1H, t, $J_{H3',H4'}$ 10.0, H-3'), 5.42 (1H, d, $J_{H1',H2'}$ 4.0, H-1'), 5.43 (1H, d d, $J_{H1,F}$ 52.4, $J_{H1,H2}$ 4.8, H-1); $\delta_C$ (100 MHz, CDCl$_3$, Me$_4$Si) 20.56, 20.60, 20.62, 20.69, 20.79, 20.86 (each s, CH$_3$ groups), 61.49 (s, C-6'), 62.64 (s, C-6), 67.98 (s, C-4'), 68.60 (s, C-5'), 69.29 (s, C-3'), 70.15 (s, C-2'), 71.23 (d, $^2J_{C,F}$ 31.6, C-2), 71.97 (s, C-4), 72.29 (s, C-5), 74.02 (d, $^3J_{C,F}$ 5.3, C-3), 95.90 (s, C-1'), 105.46 (d, 1$J_{C,F}$ 219.7, C-1), 169.36, 169.43, 169.98, 170.04, 170.45, 170.55 (each s, C=O groups); $\delta_F$ (376 MHz, CDCl$_3$, Me$_4$Si) −131.9 ppm (d d, $^1J_{H,F}$ 52.6, $^2J_{H,F}$ 8.3, F-1); m/z (Cl$^+$, NH$_3$) 656 (M$^+$+18, 52%).

EXAMPLE 9

Preparation of α-D-mannopyranosyl fluoride tetraacetate

In a similar reaction to that described in Example 7, but using phenyl-1-thio-D-mannopyranoside tetraacetate as the starting material, $^{19}$F nmr analysis of the product mixture obtained showed the presence of only the α anomer. Purification of the product mixture by column chromatography on silica gel with ethyl acetate: petroleum ether (1:1) as eluant yielded pure α-D-mannopyranosyl fluoride tetraacetate (265mg, 47%) as a clear oil; R$_F$ 0.52; $\delta_H$ (400 MHz, CDCl$_3$, Me$_4$Si) 2.1, 2.3, 2.6 and 2.9 ppm (each 3H, s, CH$_3$ groups), 4.12–4.20 (2H, m, H-5 and H-6a), 4.30 (1H, d d, $J_{6a,6b}$ 12.8, $J_{5,6b}$ 5.2, H-6b), 5.32–5.36 (2H, m, H-3 and H-4), 5.40 (1H, m, H-2), 5.58 (1H, d d, $J_{H1,F}$ 48.4, $J_{H1,H2}$ 2.0, H-1); $\delta_F$ (235 MHz, CDCl$_3$, CFCl$_3$) −138.8 ppm (d, $J_{H,F}$ 46.4, F-1) ; $\delta_C$ (100 MHz, CDCl$_3$, Me$_4$Si) 20.54, 20.60 and 20.67 ppm (each s, CH$_3$ groups), 61.83 (s, C-6), 64.99 (s, C-4), 67.63 (d, $^2J_{C,F}$ 39.3, C-2), 68.13 (s, C-5), 70.05 (d, $^3J_{C,F}$ 3.0, C-3), 104.70 (d, $^1J_{C,F}$ 223.9, C-1), 169.53, 169.62, 169.69 and 170.53 (each s, C=O groups)

EXAMPLE 10

Preparation of β-D-galactopyranosyl fluoride tetraacetate

In a similar reaction to that described in Example 7, but using phenyl-1-thio-β-D-galactopyranoside tetraacetate as the starting material, $^{19}$F nmr analysis of the product mixture obtained showed the presence of only α and β anomers in ratio α:β 1:7. Purification of the product mixture by column chromatography on silica gel with ethyl acetate: petroleum ether (1:1) as eluant yielded pure β-D-galactopyranosyl fluoride tetraacetate (300 mg, 51%) as a clear oil; R$_F$ 0.45; $\delta_H$ (400 MHZ, CDCl$_3$, Me$_4$Si) 4.06 (1H, t, $J_{5,6}$ 6.4, H-5), 4.21 (2H, d d, $J_{5,6}$ 6.6, $J_{6a,6b}$ 1.6, H-6) 5.05 (1H, d d, $J_{2,3}$ 10.4, $J_{3,4}$ 3.2, H-3), 5.26 (1H, d d, $J_{H,F}$ 54.0, $J_{1,2}$ 7.2, H-1), 5.42 (1H, m, H-4), 5.31 (1H, m, H-2); $\delta_F$ (235 MHz, CDCl$_3$, CFCl$_3$) −143.11 ppm (d d, $J_{H,F}$ 54.0 $J_{H,F}$ 12.0); $\delta_C$ (100 MHz, CDCl$_3$, Me$_4$Si) 20.53, 20.60 and 20.67 ppm (each s, CH$_3$ groups), 1.29 (s, C-6), 66.37 (s, C-4), 68.75 (d, $^2J_{C,F}$ 24.8, C-2), 69.89 (d, $^3J_{C,F}$ 10.7, C-3), 71.17 (d, $^3J_{C,F}$ 4.5, C-5), 107.08 (d, $^1J_{C,F}$ 218.6, C-1).

What is claimed is:

1. A process for the preparation of a fluorinated organic compound comprising reacting a precursor of said organic compound, said precursor containing at least one carbon bonded to a Group VI element selected from the group consisting of sulfur, selenium and tellurium, with a fluorinating agent and another halogenating agent, said fluorinating agent comprising fluorine (F$_2$), wherein fluorination occurs at said carbon.

2. A process as in claim 1 wherein said precursor comprises a thiocarbonyl containing substrate.

3. A process as in claim 1 wherein said precursor is contained in an inert solvent.

4. A process as in claim 1, wherein said halogenating agent is selected from the group consisting of elemental iodine, bromine and an interhalogen compound comprising iodine monochloride or iodine monobromide.

5. A process as in claim 1, wherein said reaction is carried out at a temperature in the range of −60° C. to +150° C.

6. A process as in claim 1, wherein said fluorinating agent is fluorine gas which is diluted before use by mixing with an inert gas such that the concentration of fluorine gas in the gaseous mixture is from 1% to 50% by volume.

7. A process for the preparation of fluorine containing compounds having a formula selected from the group consisting of:

(A)

(B)

(C)

-continued

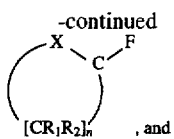 (D)

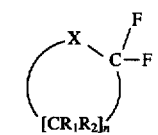 (E)

comprising reacting corresponding sulfur containing precursor compounds having formulae selected from the group consisting of:

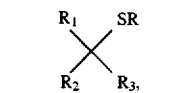 (A')

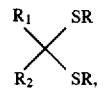 (B1')

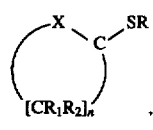 (B2')

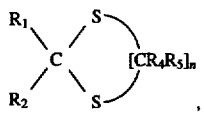 (C')

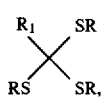 (D')

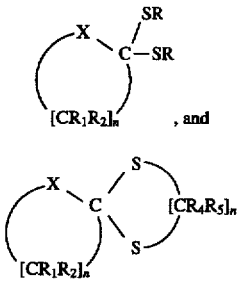 (E1')

(E2')

with fluorine ($F_2$) by the process according to claim 1;

wherein n is an integer of 1 to 8;

each of $R_1$, $R_2$, and $R_3$ is independently hydrogen, alkyl, substituted alkyl, cycloalkyl, substituted cycloalkyl, aryl, substituted aryl, or acetoxy;

each of R, $R_4$, and $R_5$ is independently hydrogen, alkyl, cycloalkyl, aryl or substituted aryl;

X is O, NR or S.

8. A process for the preparation of difluorinated compounds selected from the group consisting of:

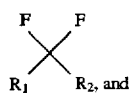 (A)

-continued

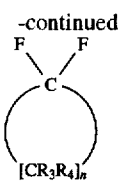 (B)

comprising reacting corresponding thiocarbonyl compounds selected from the group consisting of:

(A')

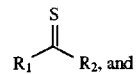 (B')

with fluorine ($F_2$) by the process according to claim 1;

wherein n is an integer of 1 to 8;

each of $R_1$, $R_2$, $R_3$ and $R_4$ is independently hydrogen, alkyl, substituted alkyl, cycloalkyl, substituted cycloalkyl, perfluoroalkyl, substituted perfluoroalkyl, aryl, substituted aryl or acetoxy.

9. A method for producing an organofluorine compound from an organic compound, comprising reacting said organic compound, said organic compound containing at least one Group VI element selected from the group consisting of sulfur, selenium and tellurium, with a fluorinating agent and another halogenating agent, said fluorinating agent comprising an elemental fluorine, wherein the rate of introduction of said fluorinating agent to a reaction mixture is controlled to retard the formation of at least one by-product.

10. The method of claim 9, wherein said rate of introduction is selected such that a molar ratio of said elemental fluorine to said organic compound ranges from about 0.5:1 to about 3.5:1.

11. The method of claim 9, wherein said elemental fluorine is diluted in an inert gas to provide a dilute gaseous mixture.

12. The method of claim 11, wherein said inert gas is selected from the group comprising helium and nitrogen.

13. The method of claim 11, wherein said inert gas is nitrogen.

14. The method of claim 12, wherein said dilute gaseous mixture comprises from about 2% to about 25% of said elemental fluorine.

15. The method of claim 12, wherein said dilute elemental fluorine comprises 10% of said elemental fluorine.

16. The method of claim 15, wherein the introduction rate of said dilute elemental fluorine is about 4.0 ml/min.

17. The method of claim 9, wherein said halogenating agent is selected from the group consisting of iodine, bromine and an interhalogen compound comprising iodine monochloride or iodine monobromide.

18. The method of claim 9, wherein the temperature of said reaction mixture is from about −60° C. to about +150° C.

* * * * *